United States Patent [19]

Breuning et al.

[11] Patent Number: 5,273,660
[45] Date of Patent: Dec. 28, 1993

[54] AMINOALKYLPHOSPHONIC ACID CONTAINING LIGANDS ATTACHED TO SOLID SUPPORTS FOR REMOVAL OF METAL IONS

[75] Inventors: Ronald L. Breuning, Orem; Bryon J. Tarbet, Highland; Jerald S. Bradshaw, Provo; Reed M. Izatt, Orem; Krzysztof E. Krakowiak, Provo, all of Utah

[73] Assignee: Brigham Young University, Provo, Utah

[21] Appl. No.: 7,075

[22] Filed: Jan. 21, 1993

Related U.S. Application Data

[62] Division of Ser. No. 774,547, Oct. 10, 1991, Pat. No. 5,182,251.

[51] Int. Cl.$^5$ .................. G01N 30/00; C02F 1/02; B01P 15/04
[52] U.S. Cl. .................. 210/670; 210/672; 210/679; 210/688; 502/401
[58] Field of Search .............. 210/679, 672, 670, 688; 502/401

[56] References Cited

U.S. PATENT DOCUMENTS

| | | | |
|---|---|---|---|
| 4,650,784 | 3/1987 | Ramsden et al. | 210/502.1 |
| 4,943,375 | 7/1990 | Bradshaw et al. | 210/679 |
| 4,952,321 | 8/1990 | Bradshaw et al. | 210/679 |
| 4,975,379 | 12/1990 | Bradshaw et al. | 210/679 |
| 5,175,110 | 12/1992 | Bradshaw et al. | 210/679 |
| 5,182,251 | 1/1993 | Bruenig et al. | 210/670 |
| 5,190,661 | 3/1993 | Bruenig et al. | 210/679 |

Primary Examiner—Stanley S. Silverman
Assistant Examiner—Cynthia L. Nessler
Attorney, Agent, or Firm—Thorpe, North & Western

[57] ABSTRACT

A method for the removal and concentration of desired ions such as $Sb^{3+}$, $Zr^{4+}$, $Zn^{2+}$, $Pu^{4+}$, $Hf^{4+}$, $Cu^{2+}$, $Ni^{2+}$, $Fe^{3+}$, $Cd^{2+}$, $Ag^+$, and $Hg^{2+}$ from a multiple ion source solution which may contain larger concentrations of other undesired ions including $H^+$ comprises bringing the source solution into contact with a compound comprising an aminoalkylphosphonic acid containing ligand covalently bonded through an organic spacer silicon grouping to a solid inorganic support. The aminoalkylphosphonic acid containing ligand portion(s) of the compound has an affinity for the desired ions to form a complex thereby removing the desired ions from the source solution. The desired ions are removed from the compound by contacting the compound with a much smaller volume of a receiving solution having a greater affinity for the desired ions than does the aminoalkylphosphonic acid containing ligand portion of the compound. The process is useful in removing desired or unwanted ions of Sb(III) from acidic waste streams, streams containing concentrated Cu(II), Ni(II), Zn(II), and Ag(I), and also the removal of Zr(IV), Pu(IV) and Hf(IV) from nitric acid solutions containing large amounts of other ions as well removal of unwanted ions from other industrial or environmental streams.

19 Claims, No Drawings

AMINOALKYLPHOSPHONIC ACID CONTAINING LIGANDS ATTACHED TO SOLID SUPPORTS FOR REMOVAL OF METAL IONS

This application is a divisional of application Ser. No. 07/774,547, filed Oct. 10, 1991, now U.S. Pat. No. 5,182,251.

FIELD OF THE INVENTION

This invention relates to aminoalkylphosphonic acid containing ligands covalently bonded to inorganic solid supports and to processes for removing, separating and concentrating certain desired ions from solutions wherein such ions may be admixed with other ions which may be present in much higher concentrations by the use of such aminoalkylphosphonic acid containing ligands as supported materials. More particularly, this invention relates to a process for removing such ions from an admixture with others in solution by forming a complex of the desired ions with compounds composed of aminoalkylphosphonic acid containing ligands bonded to an inorganic matrix by flowing such solutions through a column packed with such aminoalkylphosphonic acid containing solid ligand supported materials and then selectively breaking the complex of the desired ion from the compounds to which such ion has become attached by flowing a receiving liquid in much smaller volume than the volume of solution passed through the column to remove and concentrate the desired ions in solution in the receiving liquid. The concentrated ions thus removed may then be recovered by known methods.

BACKGROUND OF THE INVENTION

Effective methods for the recovery and/or separation of particular transition and post transition metal cations from each other and from other cations from solutions thereof, admixed with chelating agents and/or other ions which may be present, represent a real need in modern technology. As specific examples, efficient and economical separation of (1) ppm levels of Sb from concentrated Cu, Ni, Zn, Ag, or other metal cations under acidic conditions; (2) separation of Zr(IV), Pu(IV), and Hf(IV) from $HNO_3$ solutions containing large amounts of other metal cations; and (3) separation of Cu, Ni, Fe, Zn, Cd, Ag, Pb and Hg as toxic wastes from potable water or industrial effluents, all represent real separations needs with presently either unsatisfactory technologies for their accomplishment, or for which more economical technologies are desired. These ions are often present at low concentrations in solutions containing other ions at much greater concentrations. Hence, there is a real need for a process to selectively concentrate and recover these ions.

It is known that molecules containing amine and phosphonic acid groups show strong and somewhat selective interactions with lanthanides, Ga, Sb, Bi, Mn, Fe, Co, Ni, Cu, Fe, Zn, Al, Hg, Pb, and Ag under mildly acidic or neutral to basic Ph conditions. These molecules also show highly specific selectivity toward Sb(III), Zr(IV) and other 4+ metal cations under acidic conditions.

The process of the invention is particularly adaptable to the removal of Sb(III) from $H_2SO_4$ streams containing high concentrations of plating metal cations such as Cu(II) and of Zr(IV) and Pu(IV) from nitric acid streams.

The products and processes described in the present invention overcome virtually all of the difficulties described above and provide an effective means for the practical separation of desired ions.

SUMMARY OF THE INVENTION

The unique properties of the aminoalkylphosphonic acid containing ligands as attached to appropriate inorganic solid supports form the basis of the present invention. The compounds, methods of synthesis and properties are described below. The invention also encompasses processes for using the compounds for the separation of desired ions.

The compounds of the present invention comprise suitable aminoalkylphosphonic acid containing ligands which are covalently bonded through a spacer grouping to a silicon atom and further covalently bonded to a solid support and are represented by the following formula:

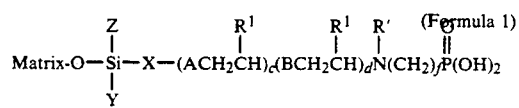

In Formula 1, A, and B are members independently selected from the group consisting of O, NR, and $N(R)CH_2$ where R and R' are members independently selected from the group consisting of

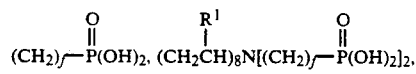

$CH_2CH_2R^1$, hydrogen, lower alkyl, aralkyl, and aryl and substituted derivatives thereof; $R^1$ is a member independently selected from the group consisting of H, SH, OH, lower alkyl, aryl, and aralkyl; c and d are each integers from 0 to about 10; and e and f are each integers from 1 to 10; X is a spacer grouping having the formula:

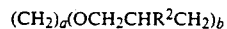

wherein $R^2$ is a member selected from the group consisting of H, SH, OH, lower alkyl, and aryl; a is an integer from 3 to about 10; b is an integer of 0 or 1. Y and Z are members independently selected from the group consisting of Cl, Br, I, alkyl, alkoxy, substituted alkyl or substituted alkoxy and O-matrix and matrix is selected from the group consisting of sand, silica gel, glass, glass fibers, alumina, zirconia, titania and nickel oxide or other hydrophilic inorganic supports and mixtures thereof. When Y and Z moieties are other than O-matrix they are functionally classified as leaving groups, i.e. groups attached to the silicon atom which, when reacted with an O-solid hydrophilic matrix material, may leave or be replaced by the O-matrix. If any such functional leaving groups are left over after reacting a silicon containing spacer group or spacer/ligand group with the solid hydrophilic matrix support material, these groups will have no direct function in the interaction between the desired ion and aminoalkylphosphonic acid group, containing ligand attached to the solid support.

Unless otherwise stated, alkyl, alkoxy, lower alkyl and lower alkoxy means 1 to 6 carbon member groups which may be substituted or unsubstituted, straight or branched chain. Also, unless otherwise stated, aryl is a member selected from the group consisting of phenyl, naphthyl and pyridyl and aralkyl is aryl to which is attached an alkyl group of one to three carbon atoms with one being preferred. Aryl and aralkyl groups may also be substituted. By substituted is meant by groups such as Cl, Br, I, $NO_2$ and the like which do not interfere with the functioning and/or operation of the compounds for the removal and separation of the desired ions.

X is a spacer grouping which is of a functional nature that it is sufficiently hydrophilic to function in an aqueous environment and will separate the ligand from the solid matrix support surface to maximize the interaction between the ligand and desired ion being separated. Representative of X are members such as glycidoxyalkyl, alkoxyalkyl, alkyl and the like.

The preferred $R^1$ grouping is H. The integers represented by e and f are preferably 1 and c and d are preferably 0 or 1.

Within the above framework, suitable subgroupings include those where X is $(CH_2)_a(OCH_2CHR^2CH_2)_b$ where a is 3 and b is an integer of 0 or 1. $R^2$ is preferably OH.

One subgrouping is where c and d are 0. This provides a ligand having at least one aminoalkylphosphonic acid group. However, R' is preferably a member selected from the group

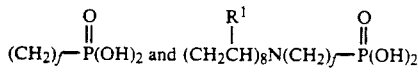

such that there are always two or more aminoalkylphosphonic groups in the ligand. Preferably the terminal nitrogen atom contains two alkylphosphonic acid groups.

Another subgrouping is where c is 1, d is 0, A is NR where R is

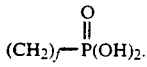

This provides a branched ligand having a terminal aminoalkylphosphonic acid group and at least one other branched aminoalkylphosphonic acid grouping. As in the above, R' is preferably a member selected from the group consisting of

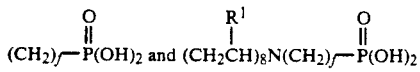

such that there are three aminoalkylphosphonic acid groups, two of which are preferably attached to the terminal nitrogen atom.

A still different subgrouping is where c and d are each 1, A is NR with R being the alkyl phosphonic acid moiety as defined above. B is also NR with R being an alkylaminoalkylphosphonic acid moiety e.g.

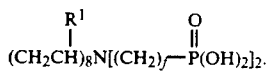

This provides a complexed branched ligand having a terminal aminoalkylphosphonic acid grouping, one branched alkylaminoalkylphosphonic acid grouping and one other branched aminoalkyl phosphonic acid grouping. As in the above, R' is preferably a member selected from the group consisting of

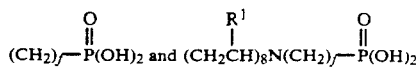

such that there are five aminoalkylphosphonic acid groups, two of which are preferably attached to the terminal nitrogen atom.

Exemplary of compounds within the above subgroupings are those wherein (1) a is 3; b is 0, c and d are 0 and f is 1 and R' is a methylphosphonic acid group, i.e. a compound containing a two aminomethylphosphonic acid groups at the terminal nitrogen wherein the ligand is attached to the silane via a propyl spacer group; (2) a is 3, b is 1, $R^2$ is OH, c is 1, d is 0, $R^1$ is H, f is 1, and A is NR wherein R and R' are the grouping,

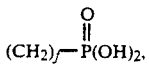

i.e. a compound containing two terminal aminomethylphosphonic acid groups and an intermediate branched aminomethylphosphonic grouping attached to the silane through a glycidyloxypropyl spacer group and; (3) a is 3, b is 0, c and d are each 1, A is NR with said R and R' both being as described in (2) above wherein B is NR with said R being a branched alkylaminoalkylphosphonic acid moiety, e.g.

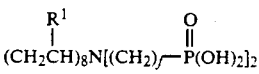

with e being 1 and f being 1 and $R^1$ being H in all occurrences, i.e. a compound containing two terminal aminomethylphosphonic acid groups, an intermediate branched ethylaminodi[methylphosphonic acid] grouping and one other branched aminomethylphosphonic acid grouping.

The aminoalkylphosphonic acid ligands covalently bonded to solid supports as shown in Formula 1 are characterized by high selectivity for and removal of desired ions or groups of desired ions such as lanthanides, Ga, Sb, Bi, Mn, Fe, Co, Ni, Cu, Zn, Al, Hg, Pb, Zr, Hf, Pu and Ag ions under mildly acidic or neutral to basic Ph conditions. These ions are usually present at low concentrations from the source phase solution containing a mixture of these metal ions with the ions one does not desire to remove (i.e. referred to as "undesired ions") present in much greater concentrations in the solution. The separation is accomplished, even in the presence of other complexing agents or matrix constituents, particularly acids, in a separation device, such as a column, through which the solution is flowed. The process of selectively removing and concentrating the desired ion(s) is characterized by the ability to quantitatively complex from a larger volume of solution the desired ion(s) when they are present at low concentrations. The desired ions are recovered from the separation column by flowing through it a small volume of a receiving phase which contains a solubilizing reagent which need not be selective, but which will strip the desired ions from the ligand quantitatively. The recovery of the desired metal ions from the receiving phase is readily accomplished by known procedures.

Moreover the terminal aminoalkylphosphonic acid ligands and, when present, other aminoalkylphosphonic acid ligands, covalently bonded to solid supports as shown in Formula 1 provide a means for separating ppm levels of Sb from concentrated Cu, Ni, Zn, Ag, or other metal cations under acidic conditions by using the separation techniques and equipment described above. The solid supported aminoalkylphosphoric acid ligands of this invention are also useful in separating Zr(IV), Pu(IV), and Hf(IV) from nitric acid solutions containing large amounts of other metal cations.

The above described solid supported ligands are effective in separating Cu, Ni, Fe, Zn, Cd, Ag, Pb and Hg as toxic wastes from potable water or industrial effluents.

DETAILED DESCRIPTION OF THE PREFERRED EMBODIMENTS

As summarized above, the present invention is drawn to novel aminoalkylphosphonic acid containing ligands covalently bound through a spacer to a silicon moiety and further attached to a solid matrix or support, to form the compounds of Formula 1. The invention is also drawn to the concentration and removal of certain desired ions such as lanthanides, Ga, Sb, Bi, Mn, Fe, Co, Ni, Cu, Zn, Al, Hg, Pb, Zr, Pu, Hf and Ag ions under mildly acidic or neutral to basic Ph conditions from other ions. For example, effective methods of recovery and/or separation of metal ions from other metal ions, such as (1) ppm levels of Sb from concentrated Cu, Ni, Zn, Ag, or other metal cations under acidic conditions; (2) separation of Zr(IV), Pu(IV), and Hf(IV) from $HNO_3$ solution containing large amounts of other metal cations; and (3) separation of Cu, Ni, Fe, Zn, Cd, Ag, Pb and Hg as toxic wastes from potable water or industrial effluents for which there are no feasible and established procedures or for which more economical processes are desired. Such solutions from which such ions are to be concentrated and/or recovered are referred to herein as "source solutions." In many instances the concentration of desired ions in the source solutions will be much less than the concentration of other or undesired ions from which they are to be separated.

The concentration of desired ions is accomplished by forming a complex of the desired ions with a compound shown in Formula 1 by flowing a source solution containing the desired ions through a column packed with a Formula 1 compound to attract and bind the desired ions to the ligand portion of such compound and subsequently breaking the ligand compound-complex by flowing a receiving liquid in much smaller volume than the volume of source solution passed through the column to remove and concentrate the desired ions in the receiving liquid solution. The receiving liquid or recovery solution forms a stronger complex with the desired ions than does the ligand portion of a Formula 1 compound and thus the desired ions are quantitatively stripped from the ligand in concentrated form in the receiving solution. The recovery of desired ions from the receiving liquid is accomplished by known methods.

The aminoalkylphosphonic acid containing ligand compounds, as represented by Formula 1, may be prepared by various methods which are illustrated in the examples which follow.

EXAMPLE 1

In this example a compound having a terminal ligand aminodi[methylphosphonic acid] group was immobilized on silica gel using the following procedure. First aminopropyl-triethoxysilane (20 g) and phosphorus acid (two equivalents) are dissolved in 400 Ml of 50% Hcl. The mixture is heated to reflux and 31 g of a 37% solution of formaldehyde is added slowly. The addition is complete within 2 hours and the mixture is cooled below the reflux temperature and 180 g of silica gel are added. The mixture is stirred mechanically, and kept between 70°-95° C. for an additional 3-18 hrs. The silica gel is filtered, washed, and air dried. This procedure results in a terminal aminodi[methylphosphonic acid] group immobilized on the silica gel surface. This compound corresponds to Formula 1 wherein the ligand is made up such that c and d are 0 and f is 1. The spacer X is $(CH_2)_a(OCH_2CHR^1CH_2)_b$ with a being 3 and b being 0. Y and Z are either O-matrix or ethoxy. This compound has the formula:

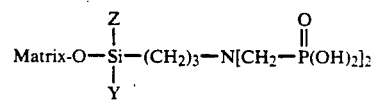

wherein Y and Z are either O-matrix or methoxy.

EXAMPLE 2

In this example the procedure of Example 1 was followed except that only one equivalent of phosphorus acid was used. This results in a single aminomethylphosphonic acid group where c and d are 0, f is 1 and the spacer X is propyl. This compound has the formula:

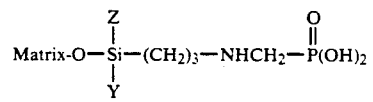

wherein Y and Z are either O-matrix or methoxy.

EXAMPLE 3

In this example a different ligand attached to a solid support was prepared containing three aminomethylphosphonic acid groupings with two being on the terminal nitrogen atom. First ethylenediamine (2.5 g) is reacted in methanol at room temperature with 3-glycidoxypropyltrimethoxysilane for 18 hrs. Next, 200 ml of a 50% HCl solution, and 3 equivalents of phosphorus acid are added and the mixture heated to reflux. Again the formaldehyde is slowly added using a 100% excess. The silica gel is added after the temperature is lowered and the product is isolated by filtration. This process results in a compound having three aminomethylphosphonic acid groupings. The compound prepared corresponds to Formula 1 wherein the c is 1, d is 0, A is NR where R and R' are both

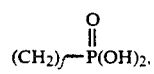

f is 1, $R^1$ is H. The spacer X is $(CH_2)_a(OCH_2CHR^1CH_2)_b$ with a being 3, being 1 and $R^1$ being OH. Y and Z are either O-matrix or methoxy. This compound has the formula:

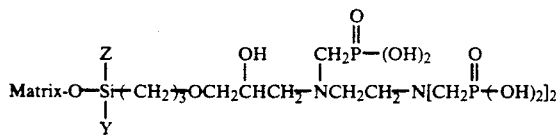

wherein Y and Z are either O-matrix or methoxy.

EXAMPLE 4

Using procedures similar to those contained in Examples 1 and 2 a complex ligand containing five aminomethylphosphonic acid groups is prepared such that c and d are each 1, A is NR and B is NR with each R being respectively the following groupings:

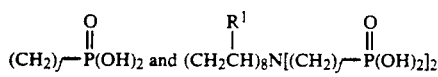

wherein $R^1$ is H, e is 1 and f is 1 and R' is a methylphosphonic acid grouping. X is such that a is 3 and b is 0. This compound has the formula:

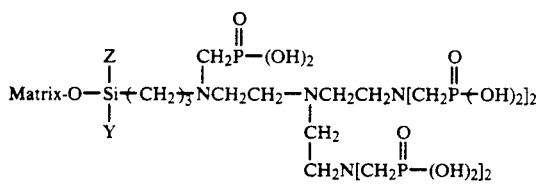

The process of selectively and quantitatively concentrating and removing a desired ion or group of desired ions presented at low concentrations from a plurality of other undesired ions in a multiple ion source solution in which the undesired ions, along with acid(s) and other chelating agents may be present at much higher concentrations, comprises bringing the multiple ion containing source solution into contact with an aminoalkylphosphonic acid ligand-containing solid supported compound as shown in Formula 1 which causes the desired ion(s) to complex with the aminoalkylphosphonic acid containing ligand portion of the compound and subsequently breaking or stripping the desired ion from the complex with a receiving solution which forms a stronger complex with the desired ions than does the aminoalkylphosphonic acid containing ligand or which forms a stronger complex with the aminoalkylphosphonic acid containing ligand. The receiving or recovery solution contains only the desired ions in a concentrated form.

The aminoalkylphosphonic acid containing ligand solid matrix support functions to attract the desired ions (DI) according to Formula 2:

$$(Matrix\text{-}O)_{1\text{-}3}\text{-}Si\text{-}X\text{-}L + DI \rightarrow (Matrix\text{-}O)_{1\text{-}3}\text{-}Si\text{-}X\text{-}L\text{:}DI \quad \text{(Formula 2)}$$

Except for DI, Formula 2 is an abbreviated form of Formula 1 wherein L stands for the aminoalkylphosphonic acid containing ligand. DI stands for desired ion being removed. When Matrix-O is less than three the other positions are taken by Y and Z groups as described above.

Once the desired ions are bound to the aminoalkylphosphonic acid containing ligand, they are subsequently separated by use of a smaller volume of a receiving liquid according to Formula 3:

$$(Matrix\text{-}O)_{1\text{-}3}\text{-}Si\text{-}X\text{-}L\text{:}DI + RL \rightarrow (Matrix\text{-}O)_{1\text{-}3}\text{-}Si\text{-}X\text{-}L + RL\text{:}DI \quad \text{(Formula 3)}$$

where RL stands for the receiving liquid.

The preferred embodiment disclosed herein involves carrying out the process by bringing a large volume of the source multiple ion solution, which may contain hydrogen ions and/or may also contain chelating agents, into contact with an aminoalkylphosphonic acid containing ligand-solid support compound of Formula 1 in a separation column through which the mixture is first flowed to complex the desired metal ions (DI) with the aminoalkylphosphonic acid containing ligand-solid support compound as indicated by Formula 2 above, followed by the flow through the column of a smaller volume of a receiving liquid (RL), such as aqueous solutions of thiourea, $NH_4OH$, $Na_2S_2O_3$, $H_2SO_4$, HCl, HI, HBr, NaI, ethylenediamine, $Na_4EDTA$, glycine and others which form a stronger complex with the desired ion than does the aminoalkylphosphonic acid containing ligand bound to the solid support or forms a stronger complex with the aminoalkylphosphonic acid containing ligand bound to solid support than does the desired ion. In this manner the desired ions are carried out of the column in a concentrated form in the receiving solution as indicated by Formula 3. The degree or amount of concentration will obviously depend upon the concentration of desired ions in the source solution and the volume of source solution to be treated. The specific receiving liquid being utilized will also be a factor. Unless otherwise required, the receiving liquid does not have to be specific to the removal of the desired ions because no other ions will be complexed to the ligand. Generally speaking the concentration of desired ions in the receiving liquid will be from 20 to 1,000,000 times greater than in the source solution. Other equivalent apparatus may be used instead of a column, e.g., a slurry which is filtered which is then washed with a receiving liquid to break the complex and recover the desired ion(s). The concentrated desired ions are then recovered from the receiving phase by known procedures.

Illustrative of desired ions which have strong affinities for aminoalkylphosphonic acid containing ligands bound to solid supports are lanthanides, $Sb^{3+}$, $Zr^{4+}$, $Zn^{2+}$, $Pu^{4+}$, $Hf^{4+}$, $Cu^{2+}$, $Ni^{2+}$, $Fe^{3+}$, $Cd^{2+}$, $Ag^+$, and $Hg^{2+}$. This listing of preferred ions is not comprehensive and is intended only to show the types of preferred ions which may be bound to aminoalkylphosphonic acid containing ligands attached to solid supports in the manner described above. The affinity of the ligand to the ions will obviously vary depending upon the ion and the ligand configuration. Hence it is possible that, even in the above listing, those ions having the stronger affinity for the ligand will be selectively removed from other ions in the listing which have a weaker affinity for the particular ligand. Hence, by proper choice of ligands and makeup of the source solution it is also possible to separate and concentrate one desired ion from another. Therefore, the terminology "desired ions" and "undesired ions" is relative and the ion having the stronger affinity to the ligand will generally be the "desired" ion.

The process of the invention is particularly adaptable to the removal of Sb(III) ions from source solutions which additionally contain Cu(II), Ni(II), Zn(II) and/or Ag(I), under acidic conditions. In these instances, the receiving liquid for removing the ion(s) bound to the ligand will preferably be 6M HCl.

REMOVAL OF DESIRED MOLECULES WITH LIGAND-MATRIX COMPOUNDS

The following examples demonstrate how the aminoalkylphosphonic acid containing ligand bound to a solid support compound of Formula 1 may be used to concentrate and remove desired ions. The aminoalkylphosphonic acid containing ligand containing solid support compound is placed in a column. An aqueous source solution containing the desired ion or ions, in a mixture of other undesired ions and/or chelating agents which may be in a much greater concentration, is passed through the column. The flow rate for the solution may be increased by applying pressure with a pump on the top or bottom of the column or applying a vacuum in the receiving vessel. After the source solution has passed through the column, a much smaller volume of a recovery solution, i.e. an aqueous solution, which has a stronger affinity for the desired ions than does the ligand, is passed through the column. This receiving solution contains only the desired ion(s) in a concentrated form for subsequent recovery. Suitable receiving solutions can be selected from the group consisting of HCl, HBr, thiourea, NaI, HI, $NH_4OH$, ethylenediamine, $Na_4EDTA$, $H_2SO_4$, $Na_2S_2O_3$, glycine and mixtures thereof. The preceding listing is exemplary and other receiving solutions may also be utilized, the only limitation being their ability to function to remove the desired ions from the aminoalkylphosphonic acid containing ligand.

The following examples of separations and recoveries of ions by the inorganic support-bound aminoalkylphosphonic acid containing ligands which were made as described in Examples 1 through 4 are given as illustrations. These examples are illustrative only, and are not comprehensive of the many separations of ions that are possible using the materials of Formula 1. However, separation of other desired ions may be accomplished as in the following examples and the exact process or procedure to be followed can be readily determined by one skilled in the art.

EXAMPLE 5

In this example, 10 g of the aminomethylphosphonic acid ligand of Example 1 was placed in a column. A 70° C., 100 ml source solution of 290 ppm (parts per million) Sb(III), 60 ppm Bi(III) and 30 g/l Cu(II) in 2M $H_2SO_4$ was drawn through the column. A 25 ml aqueous solution of 0.1M $H_2SO_4$ at 70° C. was then passed through the column to wash out the loading solution remaining in the column. The Sb was then eluted with 20 ml of 70° C., 6M HCl. Analysis of the above solutions by Inductively Coupled Plasma Spectroscopy (ICP) showed that greater than 98% of the Sb(III) originally in the 100 ml solution described above was in the 20 ml receiving solution. Furthermore, the Cu level in the receiving liquid was less than 1 ppm and the Bi(III) level was only 3 ppm.

EXAMPLE 6

The experiment of Example 4 was repeated with 10 g of the diaminotrimethylphosphonic acid ligand of Example 3. Virtually identical results were obtained.

EXAMPLE 7

In this example, 2 g of the diaminotrimethylphosphonic acid ligand of Example 3 was placed in a column. A 100 ml source solution of 10 ppm Cu(II) and 0.1M NaCl with a pH of $\approx$ 6 was drawn through the column. A 5 ml aqueous solution of 1M HCl was then passed through the column as a receiving liquid for the Cu(II). Analysis of the above solutions by ICP showed that over 99% of the Cu originally in the 100 ml solution described above was in the receiving solution.

EXAMPLE 8

This example is the same as Example 7 above except 2 grams of the material from Example 2 were used. Virtually identical results were obtained.

EXAMPLE 9

In this example, 10 g of the ligand of Example 1 was placed in a column. A 100 ml source solution of 200 ppm Zr(IV) in 5M $HNO_3$ was drawn through the column. A 25 ml aqueous solution of 0.1M $HNO_3$ was then passed through the column as a wash. Then a 25 ml aqueous solution of 0.3M $Na_4EDTA$ was passed through the column to collect the Zr. Analysis of the above solutions by ICP showed that over 99% of the Zr originally in the 100 ml solution described above was in the receiving solution.

From these examples it will be appreciated that the aminoalkylphosphonic acid containing ligands of Formula 1 bonded to a solid support, such as silica gel, provide materials useful for the separation and concentration of ions as identified above from mixtures of these ions with other metal ions. This recovery may be accomplished even in the presence of acids and/or complexing agents. The ions of interest can then be recovered from the concentrated recovery solution by standard techniques known in the science of these materials.

Although the invention has been described and illustrated by reference to certain specific silica gel-bound aminoalkylphosphonic acid containing ligands falling within the scope of Formula 1 and the process of using them, other analogs of these aminoalkylphosphonic acid containing ligand compounds also falling within the scope of Formula 1 are also within the scope of the invention as are processes of using them to separate and recover desired ions. The invention is therefore limited only in scope by the following claims and functional equivalents thereof.

We claim:

1. A method for the concentration, removal and separation of desired ions from a multiple ion source solution, which may also contain hydrogen ions and/or chelating agents, which comprises,
   (a) bringing said multiple ion source solution having a first volume into contact with an aminoalkylphosphonic acid containing ligand-solid support compound of the formula:

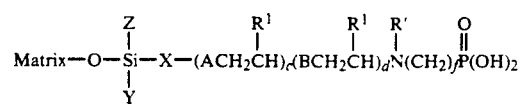

wherein A, and B are members independently selected from the group consisting of O, NR, and N(R)CH$_2$ where R and R' are members independently selected from the group consisting of

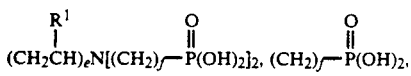

CH$_2$CH$_2$R$^1$, hydrogen, lower alkyl, aralkyl, and aryl and substituted derivatives thereof; R$^1$ is a member independently selected from the group consisting of H, SH, OH, lower alkyl, aryl, and aralkyl; c and d are each integers from 0 to about 10; e and f are each integers from 1 to 10; X is a spacer grouping having the formula:

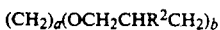

wherein R$^2$ is a member selected from the group consisting of H, SH, OH, lower alkyl, aryl and aralkyl and substituted derivatives thereof; a is an integer from 3 to about 10; b is an integer of 0 or 1; Y and Z are members independently selected from the group consisting of Cl, Br, I, alkyl, alkoxy, substituted alkyl or substituted alkoxy and O-matrix; and matrix is selected from the group consisting of sand, silica gel, glass, glass fibers, alumina, zirconia, titania and nickel oxide or other hydrophilic inorganic supports and mixtures thereof;

(b) removing source solution from contact with said compound to which said desired ions have been complexed; and (c) contacting said compound having desired ions complexed thereto with a volume, smaller than said first volume, of a receiving solution having either a greater affinity for said desired ions than said compound or a greater affinity for said compound than said desired ions thereby breaking said complex between said compound and said desired ions and recovering the desired ions in concentrated form in said smaller volume of said receiving solution.

2. A method according to claim 1 wherein said compound is contained in a packed column and wherein said multiple ion source solution is first flowed through said packed column to allow the formation of a complex between said desired ions and said compound followed by the breaking of said desired ions from said compound and removal of said desired ions from said packed column by flowing said receiving solution through said packed column and recovering said desired ions in said receiving solution in concentrated from.

3. A method according to claim 2 wherein said receiving solution is any solution having properties which allow for the desired ions to be broken from said compound.

4. A method according to claim 1 wherein the desired ions to be separated are selected from the group consisting of Sb$^{3+}$, Zr$^{4+}$, Zn$^{2+}$, Pu$^{4+}$, Hf$^{4+}$, Cu$^{2+}$, Ni$^{2+}$, Fe$^{3+}$, Cd$^{2+}$, Ag$^+$, Bi$^{3+}$, Al$^{3+}$, Ga$^{3+}$, Hg$^{2+}$ and lanthanides.

5. A method according to claim 4 wherein R' is H, c and d are 0 and f is 1.

6. A method according to claim 4 wherein R' is

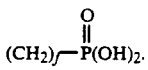

7. A method according to claim 6 wherein Sb$^{3+}$ is separated from a multiple ion source solution also containing an undesired ion selected from the group consisting of Cu, Ni, Zn, and Ag.

8. A method according to claim 6 wherein a desired ion selected from the group consisting of Zr$^{4+}$, Pu$^{3+}$, and Hf$^{4+}$ is separated from a multiple ion source solution also containing large amounts of base metals.

9. A method according to claim 6 wherein c and d are 0.

10. A method according to claim 9 wherein f is 1, a is 3 and b is 0.

11. A method according to claim 9 wherein f is 1, a is 3, b is 1 and R$^2$ is OH.

12. A method according to claim 6 wherein c and d are each 1, R$^1$ is H, A is NR with said R being

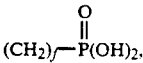

B is NR with said R being

13. A method according to claim 12 wherein e is 1, f is 1, a is 3 and b is 0.

14. A method according to claim 12 wherein e is 1, f is 1, a is 3, b is 1 and R$^2$ is OH.

15. A method according to claim 6 wherein c is 1, d is 0.

16. A method according to claim 15 wherein A is NR.

17. A method according to claim 16 wherein R$^1$ is H and R is

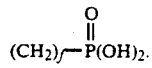

18. A method according to claim 17 wherein f is 1, a is 3 and b is 0.

19. A method according to claim 17 wherein f is 1, a is 3, b is 1 and R$^2$ is OH.

* * * * *